(12) United States Patent
Metzler et al.

(10) Patent No.: US 6,689,975 B2
(45) Date of Patent: Feb. 10, 2004

(54) FOOT CONTROLLER INCLUDING MULTIPLE SWITCH ARRANGEMENT WITH HEEL OPERATED, DOOR-TYPE SWITCH ACTUATOR

(75) Inventors: Michael E. Metzler, Eden Prairie, MN (US); Merlin Hall, Wildwood, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 10/025,424

(22) Filed: Dec. 19, 2001

(65) Prior Publication Data

US 2003/0132092 A1 Jul. 17, 2003

(51) Int. Cl.[7] .................................................. H01H 3/14
(52) U.S. Cl. ...................................... 200/86.5; 200/334
(58) Field of Search ........................... 200/86.5, 61.85, 200/334; 307/112–120

(56) References Cited

U.S. PATENT DOCUMENTS

| | | | | |
|---|---|---|---|---|
| 3,801,800 A | * | 4/1974 | Newton | 307/117 |
| 4,155,417 A | * | 5/1979 | Ziems | 200/61.85 X |
| 4,463,759 A | * | 8/1984 | Garito et al. | 307/117 X |
| 5,091,656 A | * | 2/1992 | Gahn | 307/119 |
| 5,166,513 A | * | 11/1992 | Keenan et al. | 200/86.5 X |
| 5,340,953 A | * | 8/1994 | Krebs et al. | 200/86.5 |
| 5,434,457 A | * | 7/1995 | Josephs et al. | 307/326 |
| 5,635,777 A | * | 6/1997 | Telymonde et al. | 307/119 |
| 5,712,460 A | * | 1/1998 | Carr et al. | 200/86.5 |
| 6,150,623 A | | 11/2000 | Chen | 200/86.5 |
| 2002/0045887 A1 | * | 4/2002 | DeHoogh et al. | 606/1 |
| 2003/0047434 A1 | * | 3/2003 | Hanson et al. | 200/86.5 |

* cited by examiner

*Primary Examiner*—J. R. Scott
(74) *Attorney, Agent, or Firm*—Michael L. Smith

(57) ABSTRACT

A foot controller 10 for use in ophthalmic surgery includes an accelerator-type pedal 14 for activating and controlling various surgical instruments, and a door 18 covering a switch 24. The door functions as a heel-rest when in a closed position and as a switch-shroud when in an open position.

5 Claims, 2 Drawing Sheets

FOOT CONTROLLER INCLUDING MULTIPLE SWITCH ARRANGEMENT WITH HEEL OPERATED, DOOR-TYPE SWITCH ACTUATOR

BACKGROUND OF THE INVENTION

1. Field of the Invention

The present invention relates to foot controllers for use in ophthalmic surgery.

2. Description of the Prior Art

Foot controllers for ophthalmic and other types of surgery are well-known. These foot controllers typically include an accelerator-type pedal that moves in both the vertical and horizontal directions. The movement of the accelerator pedal controls various surgical instruments and settings of the surgical system, depending on the particular operation being conducted. The foot pedal controls such things as how much power is supplied to a phacoemulsification handpiece or pneumatic scissors or vitreous cutter. In addition, such foot controllers typically include one or more additional buttons which are activated by a user pressing his foot on the button. These buttons control still further operations of the surgery equipment.

Certain surgery equipment requires a shroud to be formed around and above the switch to prevent accidental activation of the switch. Such equipment, for example, can be a surgical laser. Obviously, a user would not wish to inadvertently fire a laser pulse, and therefore, the shroud is provided. Typically, in the prior art, such shrouded switches have been separate from the main foot controller in ophthalmic surgery.

It would be highly desirable to have a foot controller with an accelerator-type pedal, such as known in the prior art, that combines a foot switch that requires a shroud. By this combination, another piece of equipment on the floor can be eliminated and the user, typically a surgeon, will always know the exact switch location.

DETAILED DESCRIPTION OF THE PREFERRED EMBODIMENT

Figure 1:
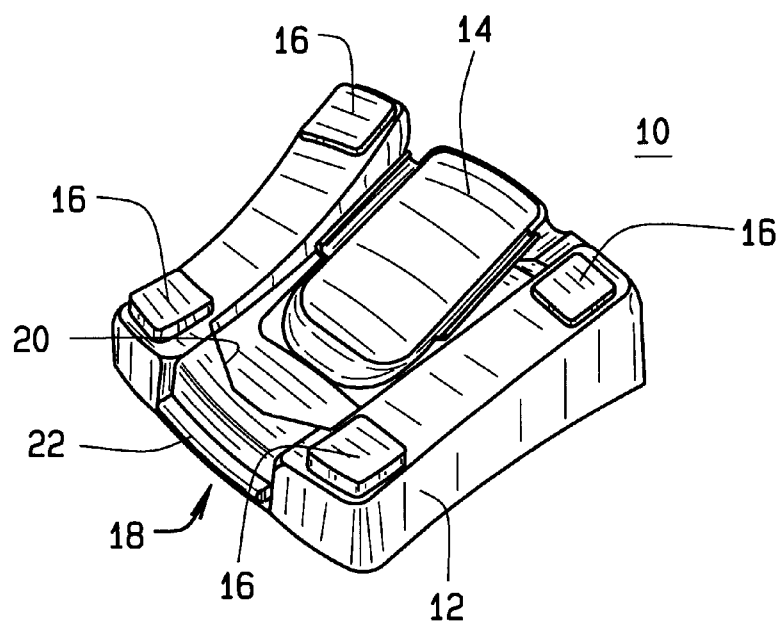
FIG. 1 illustrates a foot controller in accordance with the present invention with a door in a closed position.

FIG. 1 shows a foot controller 10, in accordance with the present invention. Foot controller 10 includes a body portion 12, an accelerator-type pedal 14, and control buttons 16. In use, foot controller 10 is typically attached to an ophthalmic surgical system, such as the Millennium® system available from Bausch & Lomb Inc. (not shown). Foot controller 10 by use of accelerator-type pedal 14 or switches 16 activates and controls various surgical instruments, as is well-known. In addition to the pedal 14 and switches 16, the present invention incorporates a door 18 covering a switch 24 (shown below). The door 18 functions as a heel-rest when in a closed position of FIG. 1, and as a switch-shroud when in an open position of FIG. 2. Preferably, door 18 includes a heel-rest ridge 20 for user comfort. In addition, door 18 preferably includes a toe-ridge 22 for allowing a surgeon to open door 18 easily. However, it is noted that foot controller 10 may have one or more doors 18 covering switches 24 and/or 16. It is not necessary that door 18 also be a heel-rest.

Figure 2:
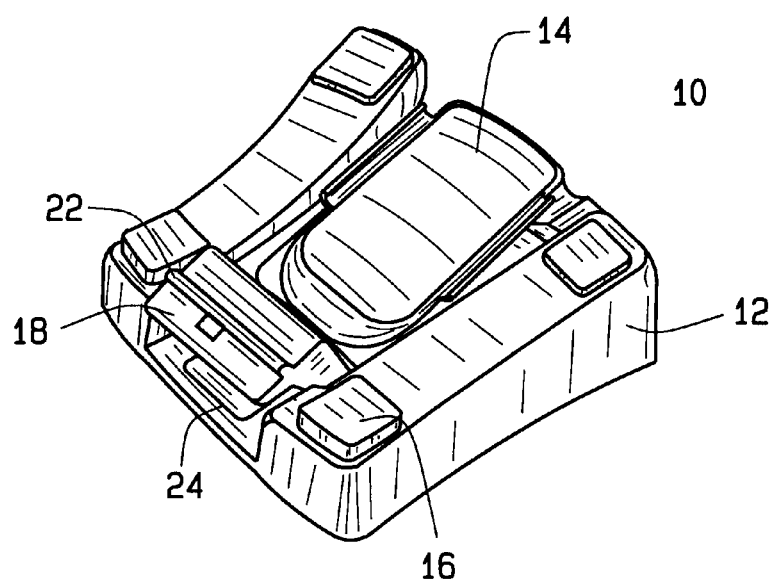
FIG. 2 illustrates a foot controller of the present invention with a door in an open position.

FIG. 2 shows foot controller 10 with door 18 in an open position. As can be seen, switch 24 controlling a surgical apparatus, such as a laser, is effectively shrouded by door 18, thereby preventing unintended activation of switch 24. Preferably door 18 is spring-loaded so that the door will automatically close unless in an open detented position.

In this way, a surgical switch 24 requiring a shroud is conveniently incorporated into an otherwise typical foot controller for use in ophthalmic surgery.

Figure 3:
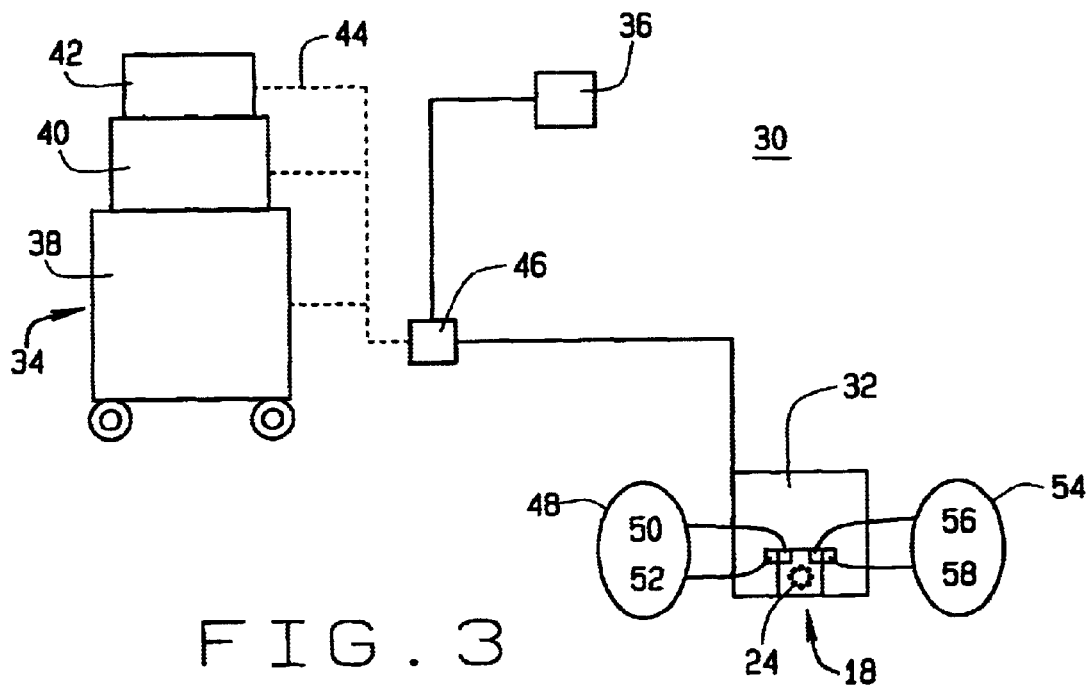
FIG. 3 is an illustration of a ophthalmic surgical system in accordance with the present invention.

FIG. 3 shows an ophthalmic surgical system 30 consisting of a foot controller 32, a surgical console 34, and optionally, a satellite foot switch 36. Surgical console 34 may consist of a cart 38, a base or control unit 40, and optionally, an expansion unit 42. Foot controller 32 and switch 36, as indicated by dashed lines 44, may be connected to any one of units 38, 40, and 42. Optional satellite foot switch 36 is shown connected to surgical console 34 via a common node 46. It should be appreciated that satellite foot switch 36 is generally dedicated to one surgical apparatus, such as a surgical laser and generally, is required to be shrouded as discussed above.

In practice, it may be desirable to have such a satellite switch 36 for the convenience of the surgeon in that, as the surgeon moves about the patient, switch 36 is more easily moved than main foot controller 32. For the sake of safety, it may be desirable to have an interlock or safety checks on foot controller 32 to ensure that switch 24 is not activated by accident.

To ensure that switch 24 is not accidentally activated on foot controller 32, it is desirable to have a door position sensor 48 for disabling activation of the surgical switch 24 except when the door 18 is in an open position. Door position sensor 48 may consist of a magnet 50 in combination with a Hall-effect IC 52 to form a Hall-effect sensor. Then, when the magnet moves to a position adjacent Hall-effect IC 52, switch 24 is enabled. For situations in which redundancy is desired, a door-presence sensor 54 for detecting when a door is present on a foot controller may also be used. Like sensor 48, sensor 54 may consist of a magnet 56 on door 18 and a Hall-effect IC 58. In much the same way as sensor 48 detects that the door is in a proper position, if sensor 54 is used, then the presence of door 18 must be detected before switch 24 is enabled. That is to say in such a redundant system, surgical switch 24 is disabled except when the door is present and open as detected by sensors 54 and 48, respectively. Requiring door 18 to be open before switch 24 is enabled prevents a foreign object being lodged between door 18 and switch 24 from activating the surgical equipment upon closure of door 18.

In a still further embodiment of the present invention, the satellite switch 36 which is separate from, but electrically connected to, the foot controller 32 may be enabled by sensors 48 and 54. In such a configuration, satellite 36 is disabled except when the door 18 is in an open position. Or, in a redundant system, satellite 36 is disabled except when the door is present and in an open position. Such a configuration may be highly desirable when console 34 includes a laser controlled by switches 24 and/or 36, since the inadvertent operation of switch 24 or switch 36 could cause serious injury to the patient or others in the operating room.

Various embodiments of an inventive surgical system 30 have been described. The disablement of foot controller 32, switch 24, and satellite switch 36 may be made from surgical console 34 with or without the use of sensors 48 and 54.

It is noted that foot controller 32 is essentially identical to foot controller 10 except that sensors 48 and 54 have been added.

Figure 4:
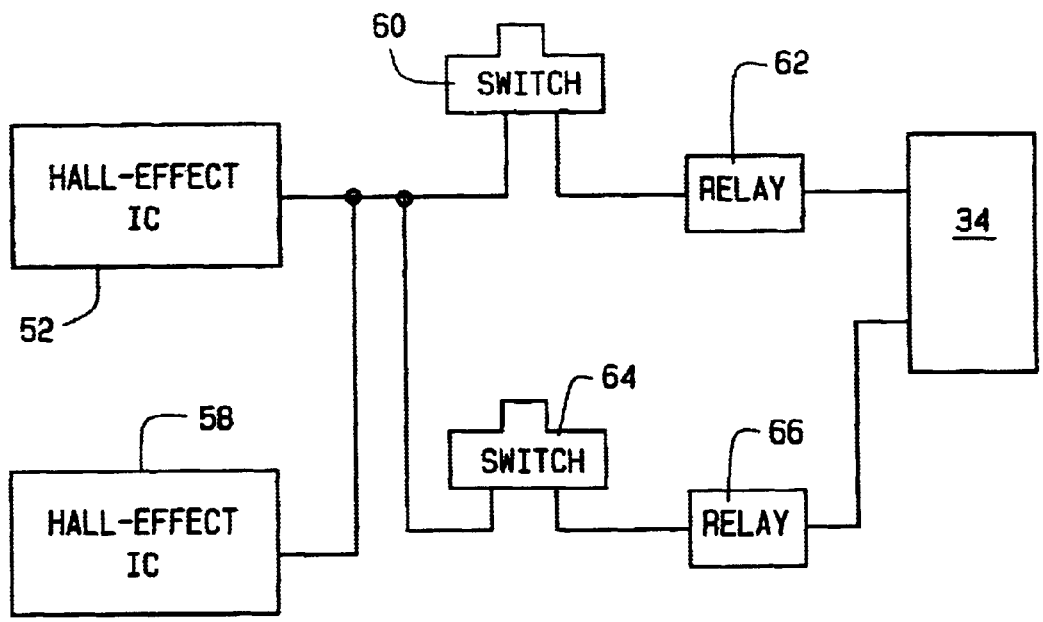
FIG. 4 is a block diagram of a switch interlock circuit in accordance with one aspect of the present invention.

FIG. 4 shows a block diagram of a circuit incorporating commercially available Hall-effect ICs 52 and 58. In addition to Hall-effect IC 52, sensor 48 includes a switch 60 (in a preferred embodiment switches 60 and 64 combine to form switch 24) which is connected to a relay 62. Switch 60 is typically electrically open and unpowered, unless Hall-effect IC 52 detects the presence of magnet 50, in which case switch 60 is powered and enabled. In an enabled state, switch 60 then controls relay 62. Relay 62 then sends an enabling signal to surgical console 34 causing the surgical instrument associated with switch 24 to operate. If redundancy is desired, Hall-effect IC 58 then cooperates with Hall-effect IC 52 to enable or disable switch 24 and/or 36.

Switch 64 and relay 66 provide redundancy for switch 60 and relay 62. In a situation where switch 60 has failed in a powered and enabled position, switch 64 and relay 66 ensure that the surgical instrument attached to switch 24 will not be enabled accidentally. In a similar fashion, Hall-effect IC 58 prevents accidental operation because of the failure of Hall-effect IC 52. Therefore, only IC 52, switch 64, and relay 62 are needed for operation of the circuit of FIG. 4. IC 58, switch 64, and relay 66 provide a measure of safety redundancy.

We claim:

1. A foot controller for use in ophthalmic surgery comprising:
    an accelerator-type pedal for activation and control of various surgical instruments; and
    a door covering a switch wherein the door functions as a heel-rest when in a closed position and as a switch-shroud when in an open position.

2. The foot controller of claim 1 wherein the door includes structure forming a recessed area for accepting a heel of a user.

3. The foot controller of claim 1 wherein the door includes a toe-ridge for allowing the door to be opened with a user's foot.

4. A foot controller for use in ophthalmic surgery comprising:
    multiple switches for activation and control of various surgical instruments;
    wherein at least one of the multiple switches is covered by a door, and such that the door functions as a switch-shroud when in an open position.

5. The foot controller of claim 4 wherein the door includes a toe-ridge for allowing the door to be opened with a user's foot.

* * * * *